US011999937B2

(12) United States Patent
Bremer, Jr.

(10) Patent No.: US 11,999,937 B2
(45) Date of Patent: Jun. 4, 2024

(54) FOAM MITIGATION IN BIOREACTORS USING ULTRASOUND

(71) Applicant: Sartorius Stedim North America Inc., Bohemia, NY (US)

(72) Inventor: Gregory Bremer, Jr., New York, NY (US)

(73) Assignee: Sartorius Stedim North America Inc., Bohemia, NY (US)

( * ) Notice: Subject to any disclaimer, the term of this patent is extended or adjusted under 35 U.S.C. 154(b) by 447 days.

(21) Appl. No.: 16/161,382

(22) Filed: Oct. 16, 2018

(65) Prior Publication Data

US 2020/0115669 A1    Apr. 16, 2020

(51) Int. Cl.
| | | |
|---|---|---|
| *C12M 3/00* | (2006.01) | |
| *C12M 1/00* | (2006.01) | |
| *C12M 1/04* | (2006.01) | |
| *C12M 1/21* | (2006.01) | |
| *C12M 1/10* | (2006.01) | |

(52) U.S. Cl.
CPC .............. *C12M 41/02* (2013.01); *C12M 1/04* (2013.01); *C12M 23/28* (2013.01); *C12M 1/10* (2013.01)

(58) Field of Classification Search
CPC .............................. C12M 41/02; C12M 41/04
See application file for complete search history.

(56) References Cited

U.S. PATENT DOCUMENTS

| | | | | |
|---|---|---|---|---|
| 4,743,361 A | * | 5/1988 | Schram ................... | A61M 1/36 209/1 |
| 2002/0039784 A1 | * | 4/2002 | Okada .................... | C12M 29/02 435/301.1 |
| 2006/0158956 A1 | * | 7/2006 | Laugharn ................ | B01F 11/02 366/127 |
| 2008/0068920 A1 | * | 3/2008 | Galliher .............. | B01F 13/0827 366/102 |
| 2013/0039810 A1 | * | 2/2013 | Riechers ................ | C12M 41/02 422/82.05 |
| 2017/0175073 A1 | * | 6/2017 | Lipkens ................. | B01D 17/06 |

FOREIGN PATENT DOCUMENTS

| | | |
|---|---|---|
| CN | 103952306 B | 9/2015 |
| CN | 106281979 B | 9/2018 |
| EP | 1179584 A1 | 2/2002 |

OTHER PUBLICATIONS

International search report for the international application No. PCT/US2019/038176.

* cited by examiner

*Primary Examiner* — Nathan A Bowers
(74) *Attorney, Agent, or Firm* — Quinn IP Law (57) ABSTRACT

A bioreactor for culturing of microorganisms or cells comprising: a casing defining an interior space of the bioreactor, wherein said interior space is configured to receive and hold a culture medium with microbial or cellular liquid cultures; and at least one coupling element provided on the casing for coupling with a foam mitigation device for mitigation of foam built-up in the interior space of the bioreactor during use of the bioreactor for culturing of microorganisms or cells; wherein the coupling element is configured to allow ultrasonic waves generated by the foam mitigation device act upon foam built-up in the interior space of the bioreactor.

17 Claims, 4 Drawing Sheets

Fig. 5

FOAM MITIGATION IN BIOREACTORS USING ULTRASOUND

TECHNICAL FIELD

The present disclosure relates to a method of foam mitigation in bioreactors using ultrasound as well as to a system for culturing of microorganisms or cells and a bioreactor suitable for said method of foam mitigation

BACKGROUND

Aerobic culturing is a common process in the fermentation industry, wherein oxygen is supplied to a culture medium in a bioreactor e.g. by ventilation and stirring. However, when large amounts of air are fed into the culture medium containing microorganisms or cells, foam generally builds up. High amount of foam may lead to clogging of filters, exhaust pipes and inlet ports. Also, microorganisms and cells adhere to the walls of the foam bubbles and get drawn out of the culture medium, which prevents proper growth of the microorganisms and cells.

Foam mitigation during culturing is commonly controlled by adding antifoam agents such as surfactants or silicone chemical agents or by a combined use of a defoaming vane and an antifoaming agent. However, these methods come along with disadvantages since the antifoaming agents are difficult to control, power costly and the productivity of microorganisms and cells in the culture medium becomes lower.

Yet another common defoaming method includes defoaming outside the bioreactor by e.g. having the foams collide with an obstruction plate or using a cyclone, and returning the defoamed culture into the bioreactor (JP-B-39-29800, JP-B-39-16041). This method usually shows lower defoaming capability, due to the presence of foam in the culture medium returned into the bioreactor. Also, the mechanical treatment negatively influences the microorganisms or cells in the culture medium.

Besides these, JP-A-5-277304, JP-A-5-317606, JP-A-7-68104 and JP-A-8-196994 describe a defoaming device using ultrasonication in a defoaming container separate from the bioreactor and a circulating pump used exclusively for this purpose, which makes the sterilization of the defoaming device ineffective. Similarly, U.S. Pat. No. 6,465,243 B2 describes using an ultrasonic horn in a pipeline between a culture tank and a liquid-vapor separating device.

All of the aforementioned defoaming methods and devices require substantial modifications of culturing systems and furthermore have negative influence on the microorganisms and cells in the culture medium.

It is therefore an object of the present invention to provide a method of foam mitigation as well as a bioreactor and a system for culturing of microorganisms or cells suitable for said foam mitigation method, which require only little effort for installation and sterilization and furthermore allows to be individually and adequately controlled depending on the process step and/or amount of foam produced in the bioreactors and which has little to no influence on the microorganisms and cells in the culture medium.

SUMMARY

One aspect of the present invention relates to a bioreactor for culturing of microorganisms or cells comprising: a casing defining an interior space of the bioreactor, wherein said interior space is configured to receive and hold a medium with microbial or cellular liquid cultures; at least one inlet port for introducing fluids into the interior space of the bioreactor; at least one outlet port for removing fluids from the interior space of the bioreactor; and a coupling element provided on the casing for coupling with a foam mitigation device for mitigation of foam built-up in the interior space of the bioreactor during use of the bioreactor for culturing of microorganisms or cells; wherein the coupling element is configured to allow ultrasonic waves generated by the foam mitigation device act upon foam built-up in the interior space of the bioreactor.

A bioreactor according to a particular embodiment comprises a casing, wherein said casing defines an interior space of the bioreactor. The bioreactor may further comprise at least one inlet port and at least one outlet port for introducing and removing fluids, i.e. liquids and/or gases. These inlet and outlet ports may include for example: A main inlet through which culture medium, cellular liquid cultures and other fluids can be introduced into the bioreactor, an exhaust air duct for avoiding gauge pressure within the bioreactor and/or for removing gases produced in the process of culturing, an outlet, preferably at or close to the bottom of the casing of the bioreactor for removing the culture medium from the bioreactor, a sample port for taking samples of the culture medium and a gas inlet for supplying gases such as oxygen to the culture medium. A bioreactor of a further particular embodiment may have one or more inlets and outlets for different purposes and in various numbers. Also, probe ports for introducing probes and/or sensors as well as a stirring device for stirring culture media inside the bioreactor may be provided.

Culture medium, according to this invention, describes one of a plurality of growth/culture media suitable for use in culturing of microorganisms or cells such as, e.g., liquids, suspensions, dispersion, homogeneous and heterogeneous mixtures and solutions.

In a further particular embodiment, the bioreactor comprises at least one coupling element. The at least one coupling element provided on the casing of the bioreactor is substantially permeable to ultrasonic waves and/or comprises a permeable part being substantially permeable to ultrasonic waves so as to allow ultrasonic waves entering the interior space of the bioreactor. The at least one coupling element may comprise materials at least partially and substantially permeable to ultrasonic waves, such as, for example, polymeric materials like polyethylene, polyurethane and acrylic glass. It is appreciated that any other suitable material may be used.

The at least one coupling element on the casing of the bioreactor is furthermore configured to be coupled with at least one foam mitigation device. Said at least one foam mitigation device is configured to reduce the amount of foam inside the bioreactor, which is produced by supplying gases such as oxygen to the culture medium in order to allow aerobic culturing of microorganisms or cells inside the culture medium. The foam mitigation device is configured to generate ultrasonic waves, which are configured to reduce foam by destroying the foam bubbles of the foam by interference of the ultrasonic waves with the foam bubbles. The ultrasonic waves generated by the at least one foam mitigation device are configured to enter the interior space of the bioreactor through the at least one coupling element to interfere with the foam. Thus, the foam is advantageously mitigated in the interior space defined by the casing of the bioreactor and not within a separate container or a pipeline, as e.g. described by JP-A-5-277304 and U.S. Pat. No. 6,465,243 B2, respectively.

The coupling element is particularly provided in a region of the casing higher than an intended filling height of the culture medium. In order to allow the ultrasonic waves to directly target the foam with no or only little interferences, the foam mitigation device and the coupling element are provided in a region of the casing which is substantially above the filling height of the culture medium in use to be introduced into the bioreactor, according to a particular embodiment. In a further particular embodiment, the coupling element is positioned on a side wall in an upper part of the casing of the bioreactor. However, the coupling element may also be provided on the upper wall/top portion of the casing of the bioreactor, preferably in close proximity to an exhaust port.

In a particular embodiment, the coupling element comprises at least an area substantially permeable to ultrasonic waves so as to allow ultrasonic waves entering the interior space of the bioreactor. In particular, at least said area of the coupling element is made of material which is substantially permeable to ultrasonic waves, such as, for example, polymeric materials like polyethylene, polyurethane and acrylic glass. It is appreciated that any other suitable material may be used.

The bioreactor may comprise one or more additional coupling elements for coupling with one or more foam mitigation devices. A plurality of coupling elements in different regions of the casing of the bioreactor allows arranging one or more foam mitigation devices in order to achieve a desired foam mitigation result. In particular, multiple coupling elements in different heights on the side wall of the casing of the bioreactor allows optimal positioning of one or more foam mitigation device(s) according to the intended filling height of the culture medium in use and/or intensity of foam generation.

In a further particular embodiment, the bioreactor is a disposable/single-use bioreactor. The casing of such a single-use bioreactor is commonly made of one or more layers of polymer foil. For example, the casing of common single-use bioreactors consists of a layer of polyethylene terephthalate or low-density polyethylene (LDPE) to provide mechanical stability, a gas barrier layer made of PVA or PVC and a contact layer from PVA or PP being in contact with the culture medium. It should be understood that any other suitable materials and compositions can be used for the casing of a disposable single-use bioreactor. Coupling elements of disposable/single-use bioreactors are in particular configured to provide a structure having sufficient mechanical stability to allow coupling with a foam mitigation device. This can, for example, be achieved by providing a frame-like structure having attachment points for coupling with a foam mitigation device. However, any other designs and arrangements suitable for providing a satisfying way of coupling of a foam mitigation device to the casing of the bioreactor may be used. A certain mechanical stability is required, in particular, to assure that a desired orientation of the foam mitigation device is maintained, respectively, a desired main propagation direction of ultrasonic waves generated by the foam mitigation device.

In a further particular embodiment, wherein the bioreactor is a multi-use bioreactor having a housing substantially made of materials with no or little permeability of ultrasonic waves, such as stainless steel or glass, the coupling element preferably covers a window/cut-out in the casing of the bioreactor substantially leak-tight. The area made of ultrasonic permeable material is thereby provided in alignment with said window/cut-out in the casing so that ultrasonic waves may by introduced into the interior space of the bioreactor through the coupling element.

Another aspect of the present invention relates to a system for culturing of microorganisms or cells comprising: a bioreactor for culturing of microorganisms or cells comprising: a casing defining an interior space of the bioreactor, wherein said interior space is configured to receive and hold a medium with microbial or cellular liquid cultures; at least one inlet port for introducing gases and/or liquids into the interior space of the bioreactor; at least one outlet port for exhausting gases and/or removing liquids from the interior space of the bioreactor; and a foam mitigation device comprising an ultrasonic wave generator for generating ultrasonic waves, wherein said ultrasonic waves are configured to act upon foam built-up in the interior space of the bioreactor during use of the bioreactor for culturing of microorganisms or cells.

Bioreactors for use in a system for culturing of microorganisms or cells according to an aspect of the invention may comprise any number and/or combinations of features and/or properties as described above.

A particular system for culturing of microorganisms or cells comprises a foam mitigation device for foam mitigation, wherein said foam mitigation device comprises at least one ultrasonic wave generator for generating ultrasonic waves. The ultrasonic wave generator is capable of generating ultrasonic waves configured to destroy foam bubbles of foam built-up inside the bioreactor in the process of culturing. Specifically, an ultrasonic wave generator for generating ultrasonic waves, suitable for foam mitigation according to an aspect of the invention, is capable of generating ultrasonic waves having a frequency between approximately 10 kHz to 1 GHz. The ultrasonic wave generator may comprise piezo-electric elements comprising quartz, berlinol, barium titanate and/or lead zirconate titanate (PZT). The ultrasonic wave generator may alternatively comprise ferromagnetic materials for generating ultrasonic waves. It is appreciated that any other material and/or structure known by the skilled person and capable of generating ultrasonic waves may be used.

In a particular system for culturing of microorganisms or cells, the foam mitigation device and, in particular, the ultrasonic wave generator is provided in a way so that ultrasonic waves generated by the ultrasonic wave generator can interfere with the foam bubbles of the foam built-up inside the bioreactor. More specifically, position and orientation of the ultrasonic wave generator allow targeting the foam inside the bioreactor.

In a particular embodiment of the system for culturing of microorganisms or cells, the bioreactor further comprises a coupling element provided on the casing of the bioreactor for coupling with a foam mitigation device for mitigation of foam built-up in the interior space of the bioreactor during use of the bioreactor for culturing of microorganisms or cells and wherein the foam mitigation device is coupled with the coupling element on an outer side of the bioreactor. Most particular, the coupling element is provided in a region of the casing higher than an intended filling height of the culture medium so as to interfere with the foam built-up inside the bioreactor above the surface of the culture medium also without significant obstructions. The foam mitigation device may be provided with a distance to the casing.

The bioreactor may further comprise at least one inlet port for introducing fluids into the interior space of the bioreactor and at least one outlet port for removing fluids from the interior space of the bioreactor. In yet a further particular embodiment of the system for culturing of microorganisms or cells, the bioreactor is a disposable/single-use bioreactor having a casing made of e.g. one or more layers of polymer foil. Suitable materials include, amongst others, polyethylene terephthalate, low-density polyethylene, PVA, PVC, PVA and PP. The coupling element of disposable/single-use bioreactor is configured to provide a coupling structure suitable to couple the foam mitigation device. Alternatively, wherein the bioreactor is a multi-use bioreactor having a housing substantially made of materials with no or little permeability of ultrasonic waves, such as stainless steel or glass, the coupling element preferably covers a window/cut-out in the casing of the bioreactor substantially leak-tight. The area made of ultrasonic permeable material is thereby provided in alignment with said window/cut-out in the casing so that ultrasonic waves generated by the ultrasonic wave generator may by introduced into the interior space of the bioreactor by passing through the coupling element.

In a further particular embodiment of a system for culturing of microorganisms or cells according to an aspect of the present invention, the ultrasonic wave generator is rotatable and/or movable relative to the bioreactor. In particular when using bioreactors having a large interior space and/or a large diameter, it might be difficult to achieve satisfying foam mitigation results using a single foam mitigation device since the ultrasonic waves generated by the ultrasonic wave generator of the single foam mitigation device are only able to act upon foam in a certain region of the interior space of the bioreactor. Therefore, a rotatable/pivotable foam mitigation device and/or ultrasonic wave generator allow changing the focus point and/or main direction of propagation of the ultrasonic waves used to destroy the foam bubbles of the foam. Consequently, a larger region inside the bioreactor can be targeted by the ultrasonic waves for improved foam mitigation. As an alternative and/or in combination, the foam mitigation device and/or the ultrasonic wave generator is movable relative to the bioreactor, i.e. along its circumference and/or in a vertical direction to increase the region of action of the foam mitigation device. Also, alternatively and/or in combination, different frequencies and/or intensities of the ultrasonic waves may be used. Also, generation of ultrasonic waves may occur continuously and/or in repeating bursts of ultrasonic waves. The system for culturing of microorganisms or cells may comprise a plurality of foam mitigation devices, wherein the plurality of foam mitigation devices may generate ultrasonic waves having different or identical properties and/or focal points/target regions. Also, one or more sensors may be provided for detecting the amount of foam built-up inside the bioreactor so that specific regions can be targeted and/or ultrasonic wave properties can be modified for improved foam mitigation.

In a further particular embodiment of a system for culturing of microorganisms or cells according to an aspect of the present invention, the ultrasonic wave generator of the foam mitigation device is configured to generate an ultrasonic wave beam, wherein said ultrasonic wave beam has a substantially planar fan-like shape. This shape of an ultrasonic wave beam is beneficial in that it concentrates the ultrasonic waves in a substantially planar region so as to precisely target foam along the respective substantially planar fan-shape region without influencing foam and/or substances outside of said substantially planar fan-shape region. Hence, by proper arrangement of the ultrasonic wave generator, it can be avoided that the ultrasonic waves interfere with e.g. the culture medium and/or the microorganisms or cells inside the culture medium, which could lead to a negative influence of productivity and/or growth of the microorganisms and cells. An illustration and a detailed description of this particular embodiment is provided in FIGS. 4 and 5 and the corresponding section of the description.

In yet another particular embodiment, the foam mitigation device comprises a plurality of ultrasonic wave generators. Said plurality of wave generators may be configured to generate ultrasonic waves each having different or the same ultrasonic wave properties such as focal point, wavelength, intensity and/or generation pattern. This way a large variety of foam mitigation characteristics can be provided for a variety of sizes and/or types of bioreactors and systems for culturing of microorganisms or cells.

Yet another aspect of the present invention relates to a method of foam mitigation, in particular with bioreactors and/or systems for culturing of microorganisms or cells according to aspects of the present invention, comprising the steps of: culturing of microorganisms or cells in a bioreactor, wherein the casing of the bioreactor comprises at least one permeable part being configured to allow ultrasonic waves entering the interior of the bioreactor; and generating ultrasonic waves and pointing said ultrasonic waves on foam built-up inside the bioreactor through the at least one permeable part.

The method of foam mitigation may include provision of a single-use bioreactor. The method may also include introducing a culture medium with microorganisms or cells into the bioreactor through one or more inlets/inlet ports in the casing of the bioreactor and/or supplying oxygen to the culture medium and/or stirring the culture medium.

The method of foam mitigation may further include providing one or more foam mitigation devices having one or more ultrasonic wave generators, wherein generating ultrasonic waves may include generating ultrasonic waves having a variety of patterns and properties, such as focal points, main directions of propagation, wavelengths and/or intensities.

The method of foam mitigation is not limited to a bioreactor but may also be applied to a bag for shipping, mixing, freeze and thaw, fluid storage or fluid transfer.

A bag whether used in a bioreactor or otherwise can be made of mono or multi layers of films comprising or consisting of PE (polyethylene of any grade), EVA (ethylene vinyl acetate), fluoropolymers, PP (polypropylene), PVC (polyvinyl chloride), PET (polyethylene terephthalate), EVOH (ethylene vinyl alcohol) or PA (polyamide). The present invention is further explained in detail by the following detailed description and the appended drawings, in which particular embodiments are illustrated by way of example, wherein the present invention is in no way limited by these particular embodiments.

DETAILED DESCRIPTION

Figure 1:
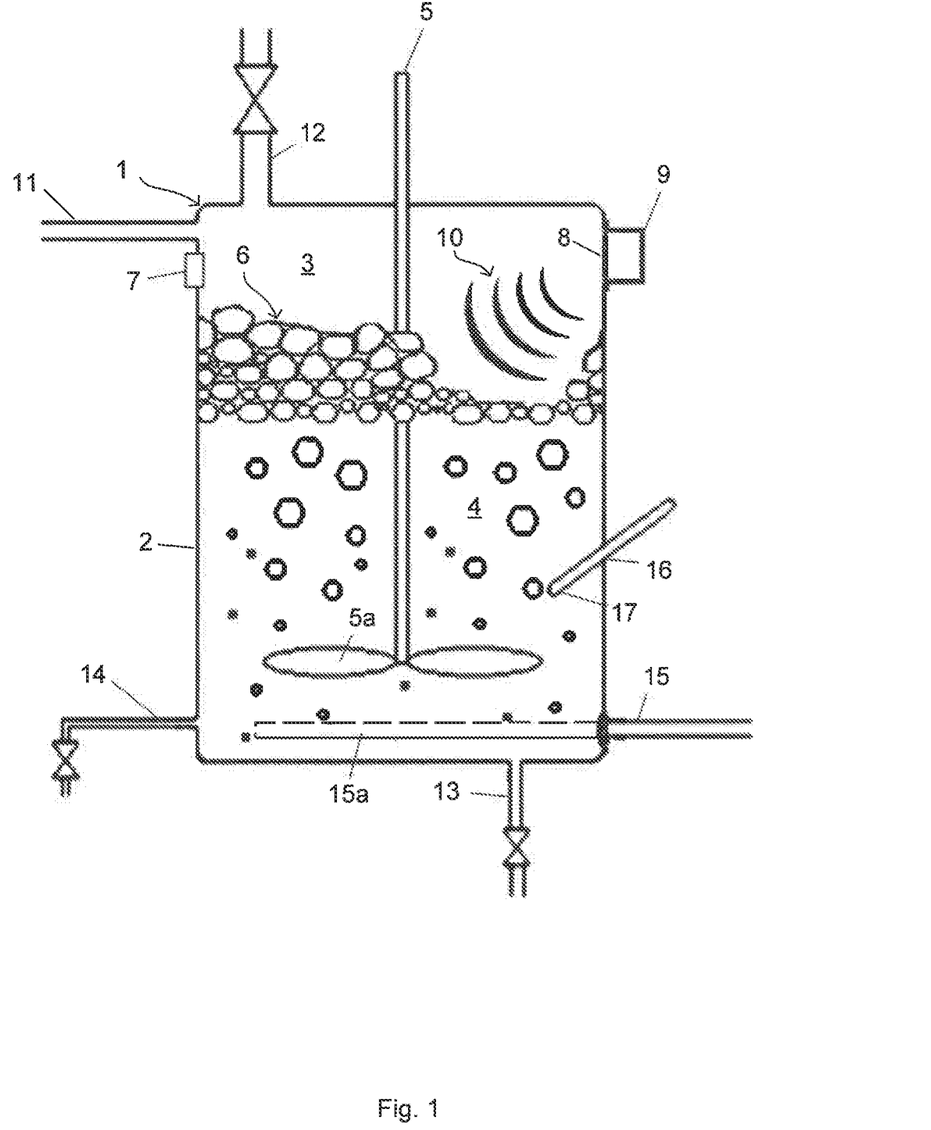
FIG. 1 shows a basic side view of an exemplary system for culturing of microorganisms or cells comprising a bioreactor and a foam mitigation device.

FIG. 1 shows a basic side view of a bioreactor 1 having a casing 2, wherein the casing defines an interior space 3 of the bioreactor 1. The bioreactor 1 can be a disposable, single-use bioreactor or a conventional, multi-use bioreactor. The interior space 3 of the bioreactor 1 has been filled with medium 4 comprising cellular liquid cultures or microorganisms. The bioreactor 1 further comprises a stirring device 5 having rotor blades 5a, wherein said stirring device 5 is configured to stir the medium 4 so that the cellular liquid cultures inside the medium 4 are substantially in continuous movement inside the bioreactor 1.

The bioreactor 1 comprises a plurality of inlet and outlets: A main inlet 11 is provided through which culture medium, cellular liquid cultures and other fluids can be introduced into the bioreactor 1. The bioreactor 1 further comprises an exhaust air duct 12 in an upper region of the casing 2 of the bioreactor 1, which is e.g. used to avoid gauge pressure within the bioreactor 1 and/or to remove gases produced in the process of culturing from inside the bioreactor 1. An outlet 13 is provided at or near the bottom of the casing 2 of the bioreactor 1 in order to remove the culture medium 4 from the bioreactor 1, e.g. after completion of the process of culturing. The bioreactor 1 further has at least one sample port 14, which e.g. allows taking samples of the culture medium 4 during culturing in order to analyze the characteristics and quality of the medium 4 and/or the cellular liquid cultures. In order to achieve aerobic culturing, at least one gas inlet 15 is provided in a lower region of the casing 2 of the bioreactor 1. Said gas inlet 15 allows continuously introducing gases such as oxygen e.g. in order to support growth and/or productivity of the cellular liquid cultures. Also, a sparger/sparger loop 15a is provided for advantageously distributing the introduced gases in the culture medium 4.

Also, the bioreactor 1 comprises at least one probe port 16 for introducing and/or arranging probes/sensors 17 for analyzing and controlling the process of culturing. Parameters of interest are for example temperature, pH-value and/or oxygen concentration.

It is to be noted that the number and specific purposes of the inlets, outlets and ports of the bioreactor 1 shown in FIG. 1 are only exemplary and can be changed, modified and/or complemented in various ways in order to meet specific requirements.

As can be seen in FIG. 1, foam 6 builds up in the bioreactor 1 in the process of culturing e.g. due to gases supplied to the culture medium 4 and/or the stirring of stirring device 5. Excessive amount of foam 6 can lead to clogging of inlets and outlets. Also, microorganisms and cells in the medium 4 adhere to the walls of the foam bubbles and thereby get drawn out of the culture medium 4. However, it is advantageous that the cells and microorganisms stay in the controlled environment within the medium 4 in order to achieve proper growing and/or productivity of the microorganisms and cells.

In order to reduce the amount of foam 6, at least one foam mitigation device 9 is coupled with at least one corresponding coupling element 8 provided on the casing 2 of the bioreactor 1. The foam mitigation device 9 is capable of generating ultrasonic waves 10, which are able to destroy foam bubbles. Specifically, the foam mitigation device 9 comprises an ultrasonic wave generator for generating ultrasonic waves 10. As an example, an ultrasonic wave generator suitable for the foam mitigation method according to the present invention is capable to generate ultrasonic waves having a frequency between 10 kHz to 1 GHz. Commonly, ultrasonic wave generators comprise piezo-electric elements such as quartz, berlinol, barium titanate or lead zirconate titanate (PZT). Alternatively, ferromagnetic materials are used for generating ultrasonic waves.

The at least one coupling element 8 of the case 2 of the bioreactor 1 is provided substantially in a region of the casing 2 of the bioreactor 1, which in use is above the filling level of the culture medium 4, and is furthermore configured to allow passing of ultrasonic waves 10 into the interior space 3 of the bioreactor 1. Therefore, when using a multi-use bioreactor, which is commonly made of stainless steel, the coupling element 8 comprises an area of material which is substantially permeable to ultrasonic waves, such as, for example, polymeric materials like polyethylene, polyurethane and acrylic glass. Due to the permeability to ultrasonic waves of the coupling element 8, ultrasonic waves 10 generated by the foam mitigation device 9 can act upon the foam 6 built-up in the interior space 3 of the bioreactor 1. The ultrasonic waves 10 destroy the foam bubbles, thereby mitigating the foam 6.

Furthermore, in the particular embodiment shown in FIG. 1, at least one foam detector 7 is provided for detection of presence, height and/or properties of foam inside the bioreactor. Such a foam detector 7 may comprise one or more of an optical, electronic (capacitive/inductive), ultrasonic, radar and/or mechanic sensor for foam detection. Signals obtained from the one or more foam detectors 7 can be used for controlling the foam mitigation device 9. For example, in case the foam detector detects no or only small amounts of foam in the interior space 3 of the bioreactor 1, e.g. the intensity and/or frequency of ultrasonic waves generated by one or more foam mitigation device 9 may be reduced and/or generating ultrasonic waves may be stopped for one or more foam mitigation devices 9. Another exemplary controlling function may include using one or more foam detectors 7 configured to detect a rate of foam produced inside the bioreactor 1. Thus, in case where an increase of the amount of foam is detected, e.g. the intensity and/or frequency of ultrasonic waves generated by one or more foam mitigation devices 7 may be increased. Alternatively and/or in addition, one or more foam mitigation devices 7 currently not generating ultrasonic waves may be activated.

It is to be appreciated that behavior and properties of the ultrasonic wave generator can be varied and/or modified to satisfy individual requirements. As an example, frequency, intensity and/or orientation (main direction of propagation) of the ultrasonic waves 10 can be adjusted to obtain satisfying results. Using higher frequencies might be advantageous for destroying smaller foam bubbles, whereas lower frequencies might be advantageous for destroying larger bubbles. Also, intensity and frequency of the ultrasonic waves can vary over time, i.e. in a repeating pattern. Alternatively and/or in combination, short bursts of ultrasonic waves can be generated with constant and/or varying repetition rates. Furthermore, various positions of the coupling element 8 on the casing 2 of the bioreactor 1 can be chosen, e.g. depending on the size of the casing and/or number and arrangement of inlets, outlets and ports. Moreover, the casing 2 of the bioreactor 1 can be provided with a plurality of coupling elements 8. Said plurality of coupling elements 8 can, for example, provide different coupling positions for a single foam mitigation device 9 for different filling heights of the culture medium 4. Alternatively and/or in combination, a plurality of foam mitigation devices 9 may be coupled to the plurality of coupling elements 8 in order to achieve foam mitigation over a large region of the interior space 3 of the bioreactor 1 and/or high concentration of ultrasonic waves in a certain region within the bioreactor 1. Also, in addition and/or as an alternative to the above modifications, the ultrasonic wave generator may be configured rotate/pivot with respect to the bioreactor 1 so that the orientation (main direction of propagation) of the ultrasonic waves 10 can change so that i.e. the waves can be focused on different regions of the interior space 3 of the bioreactor. This can also be achieved by a movable and/or rotatable reflection device which reflects the ultrasonic waves 10 in different directions.

Figure 2:
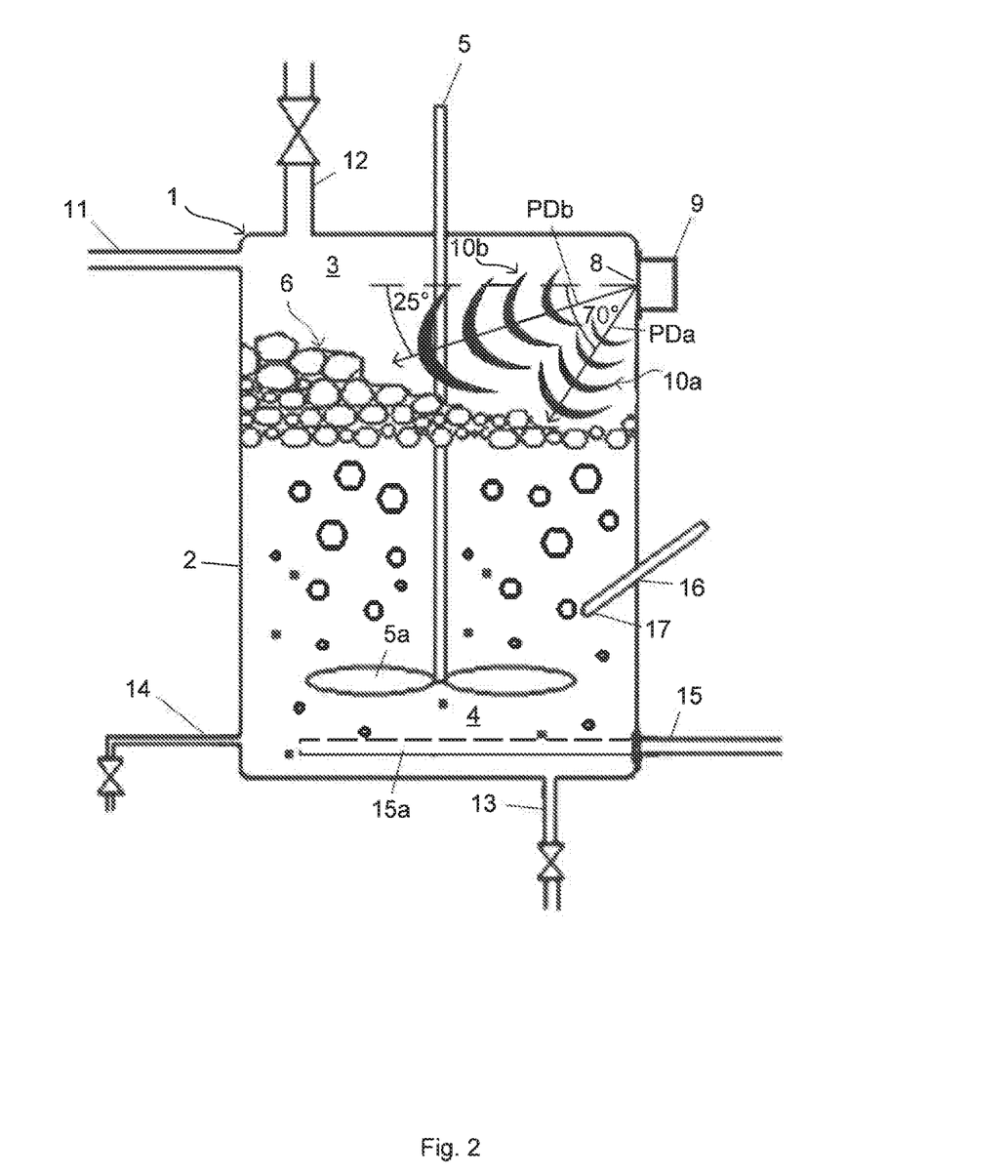
FIG. 2 shows a further exemplary system for culturing of microorganisms or cells comprising a bioreactor and a foam mitigation device, wherein the foam mitigation device comprises two ultrasonic wave generators.

FIG. 2 shows a bioreactor 1 similar to the bioreactor in FIG. 1, wherein the bioreactor 1 has a casing 2, wherein the casing defines an interior space 3 of the bioreactor 1. The bioreactor 1 can be a disposable, single-use bioreactor or a conventional, multi-use bioreactor. The interior space 3 of the bioreactor 1 contains a medium 4 with cellular liquid cultures. The bioreactor 1 further comprises a probe port 16 for introducing probes/sensors 17 and a stirring device 5 having rotor blades 5a. The bioreactor 1 comprises a main inlet 11, an exhaust air duct 12 in an upper region of the casing 2 of the bioreactor 1 and an outlet 13 at the bottom of the casing 2 of the bioreactor 1. The bioreactor 1 further has a sample port 14 for taking samples of the culture medium 4 and a gas inlet 15 for supplying oxygen to the culture medium 4. Also, a coupling element 8 for coupling with a foam mitigation device 9 is provided on the casing 2.

In contrast to the exemplary embodiment shown in FIG. 1, the embodiment shown in FIG. 2 comprises a foam mitigation device 9 having plural, e.g. two, ultrasonic wave generators. In this particular embodiment, the two ultrasonic wave generators generate a plurality of ultrasonic waves 10a, 10b with different main directions of propagation DPa, DPb. In other words, the plurality of ultrasonic wave generators have focal points different from each other and not along a common axis. More specifically, in the particular embodiment shown in FIG. 1, ultrasonic waves 10a are transmitted in a main direction of propagation DPa in an angle of approximately between 90° to 45° relative to a horizontal direction, wherein ultrasonic waves 10b are transmitted in a main direction of propagation DPb in an angle of approximately between 45° and 0°. The particular embodiment thereby increases the region of action so that foam mitigation is achieved over a larger region of the interior space 3 of the bioreactor 1. It should be understood that orientation of main propagation direction of the plurality of ultrasonic waves can be altered based on the number and/or allocation of the plurality of ultrasonic wave generators and/or size of the bioreactor and/or amount of foam inside the bioreactor in order to achieve foam mitigation in a sufficiently large region and/or in sufficient high intensity.

The embodiment shown in FIG. 2 can be varied and modified in the same ways as specified for the embodiment shown in FIG. 1. In this respect, it might be particularly advantageous to transmit the ultrasonic waves 10a, 10b with different intensities, whereas, for example, the intensity of ultrasonic wave 10b is higher than that of ultrasonic wave 10a since ultrasonic wave 10b targets foam 6 in a larger region and which is farther away than ultrasonic wave 10a. As an alternative and/or in combination, ultrasonic wave 10a could be generated in repeated bursts.

Figure 3:
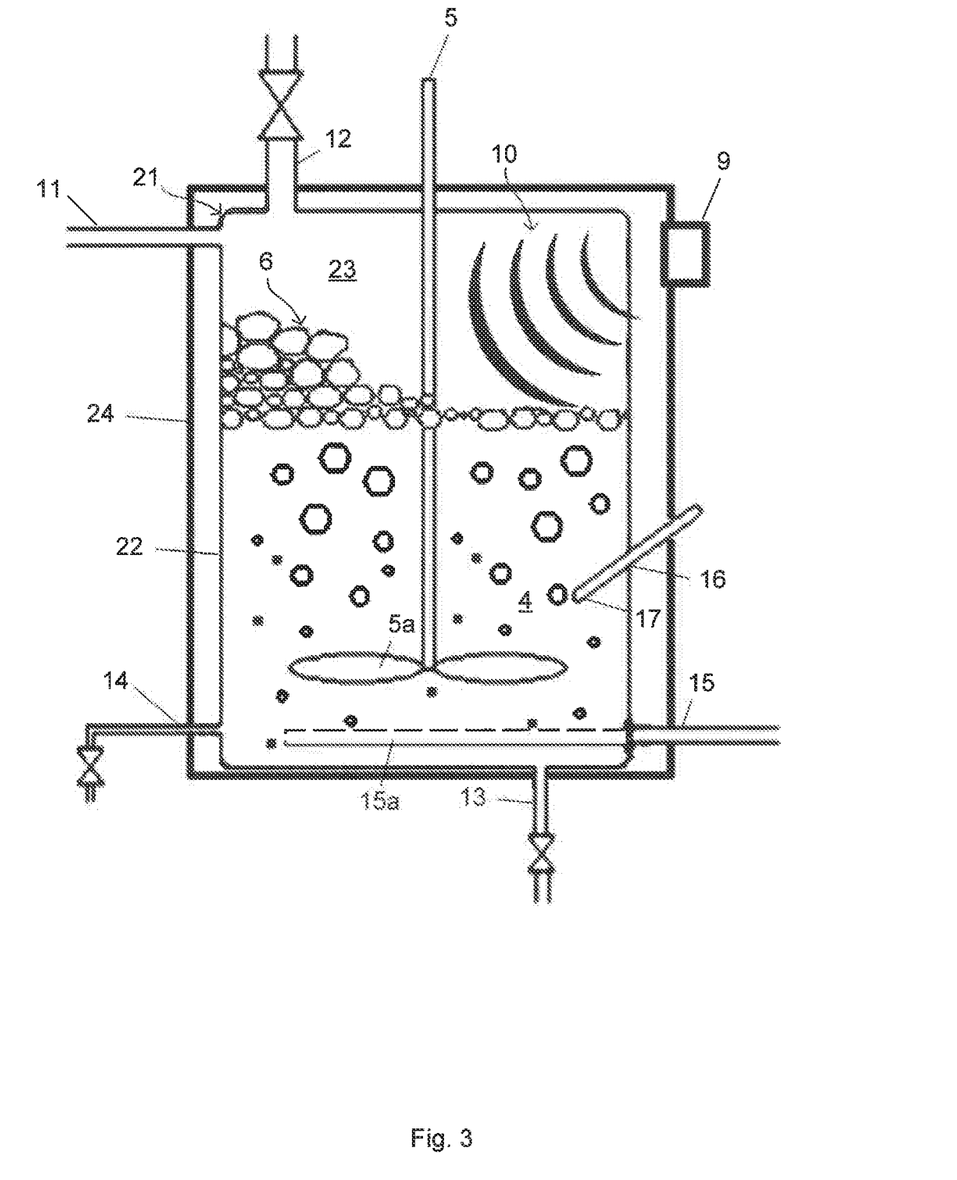
FIG. 3 shows a further exemplary system for culturing of microorganisms or cells comprising a single-use bioreactor in a bioreactor housing.

FIG. 3 shows another particular embodiment of a system for culturing of microorganisms or cells comprising a disposable, single-use bioreactor 21 having a casing 22, wherein the casing defines an interior space 23 of the bioreactor 21. The disposable, single-use bioreactor 21 is positioned within a bioreactor housing 24. The casing 22 of the disposable, single-use bioreactor 21 in this particular embodiment consists of or comprises a layer of polyethylene terephthalate or low-density polyethylene (LDPE) to provide mechanical stability, a gas barrier layer made of PVA or PVC and a contact layer from PVA or PP being in contact with the interior space 23. The bioreactor housing 24 acts as a single-use bioreactor platform, in which a single-use bioreactor 21 can be installed/mounted. The bioreactor housing 24 is further configured for stabilization of the single-use bioreactor 21 and/or tempering of the culturing medium 4 inside the bioreactor 21. The housing 24 also provides numerous passages for easy access of inlets, outlets and ports.

In order to reduce the amount of foam 6, at least one foam mitigation device 9 is provided. The at least one foam mitigation device 9 is capable of generating ultrasonic waves 10, which are able to destroy foam bubbles. Ultrasonic waves suitable for foam mitigation have a frequency in the range between kHz and several GHz and can e.g. be generated by transmitters using ferromagnetic materials or piezo-electric elements such as quartz, berlinol, barium titanate or lead zirconate titanate (PZT).

In this embodiment, the foam mitigation device 9 is provided at the bioreactor housing 24 at a distance to the casing 22 of the bioreactor 21 and in a region higher than the filling height in use of the culture medium 4 inside the bioreactor 21. The shown embodiment, however, requires that the disposable, single-use bioreactor 21 comprises an area of the casing 22 which is substantially permeable to ultrasonic waves so that the ultrasonic waves 10 generated by the foam mitigation device 9 are at least partly able to enter the interior space 23 of the bioreactor 21 and to act on the foam 6 inside the bioreactor 21. Therefore, it is advantageous using a single-use bioreactor 21 which casing 22 consists of material substantially permeable to ultrasonic waves. Alternatively, an area comprising material permeable to ultrasonic waves is provided at a region of the casing 22 which is along a line between the foam 6 and the foam mitigation device 9.

Figure 4:
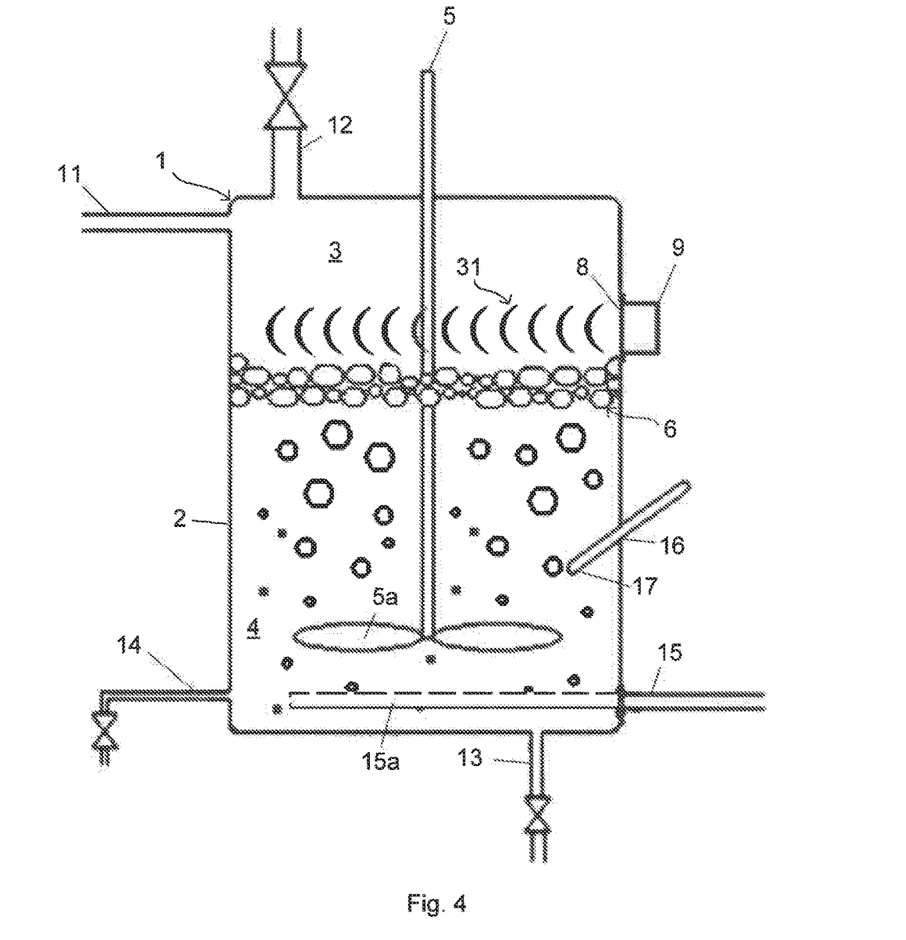
FIG. 4 shows a further exemplary system for culturing of microorganisms or cells comprising a bioreactor and a foam mitigation device, wherein the foam mitigation device generates an ultrasonic wave beam having a substantially planar fan-like shape.

FIG. 4 shows a bioreactor 1 similar to the bioreactor in FIGS. 1 and 2, wherein the bioreactor 1 has a casing 2, and wherein the casing defines an interior space 3 of the bioreactor 1. The bioreactor 1 can be a disposable, single-use bioreactor or a conventional, multi-use bioreactor. The interior space 3 of the bioreactor 1 contains a culture medium 4 with cellular liquid cultures. The bioreactor 1 further comprises a probe port 16 for introducing probes/sensors 17 and a stirring device 5. The bioreactor 1 comprises a main inlet 11, an exhaust air duct 12 in an upper region of the casing 2 of the bioreactor 1 and an outlet 13 at the bottom of the casing 2 of the bioreactor 1. The bioreactor 1 further has a sample port 14 for taking samples of the culture medium 4 and a gas inlet 15 for supplying oxygen to the culture medium 4.

However, according to this particular embodiment of the present invention, a foam mitigation device 9 is coupled to a coupling element 8 of the casing 2 of the bioreactor 1, wherein the foam mitigation device 9 is configured to generate an ultrasonic wave beam 31. Said wave beam 31 advantageously has a substantially planar fan-like shape/fan-shape and is oriented substantially horizontally, in other words, its main propagation direction is substantially horizontal. Such a wave beam 31 is advantageous in that it is able to act on foam 6 in a large region in the interior space 3 of the bioreactor 1. Accordingly, high intensity of the ultrasonic waves might be necessary to achieve sufficient foam mitigation due to the possibly large amounts of foam within the region covered by the ultrasonic wave beam. High intensity ultrasonic waves, however, potentially negatively influence growth and/or productivity of microorganisms and cells in the culture medium 4. But, due to the orientation and restricted/concentrated form of the ultrasonic wave beam 31, the high ultrasonic waves of the ultrasonic wave beam 31 do not act on the culture medium 4. Thus, no negative influence on microorganisms and cells in the culture medium 4 occurs.

Figure 5:
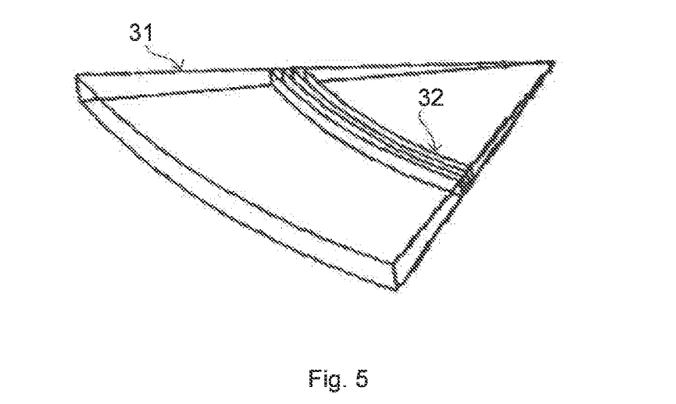
FIG. 5 shows an ultrasonic wave beam having a substantially planar fan-like shape.

Such a substantially planar fan-shaped wave beam 31 is shown in FIG. 5. Also, by way of example, FIG. 5 shows a burst 32 of ultrasonic waves propagating in a fan-shaped form.

As a matter of course, the embodiment shown in FIG. 3 and FIG. 4 can be varied and modified substantially in the same ways as specified for the embodiments of FIG. 1 and FIG. 2. In particular, rotating/pivoting of the foam mitigation device 9 relative to the bioreactor is advantageous in order to increase the region covered for foam mitigation within the bioreactor. Also, wave beams in other shapes can be used such as, for example, substantially planar linear and/or cone-shape, also in the embodiments shown in FIGS. 1-3.

It should be understood that embodiments discussed in the description and shown in the drawings only constitute illustrative exemplary embodiments of the present invention. In light of the present disclosure the person skilled in the art is offered a wide range of possible variations and combinations of individual features.

The invention claimed is:

1. A bioreactor for culturing of microorganisms or cells and for mitigating the accumulation of foam within the bioreactor via ultrasound and without the use of direct mechanical agitation, the bioreactor comprising:
   a casing defining an interior space of the bioreactor, the casing extending between a first, lower end and a second, upper end and including an intended filling height located between the first end and the second end, wherein said interior space is configured to receive and hold a culture medium with microbial or cellular liquid cultures between the lower end and the intended filling height; and
   at least one coupling element provided on the casing at a location between the intended filling height and the upper end, the coupling element adapted to receive a foam mitigation device external to the casing, the foam mitigation device being configured to emit ultrasonic waves for mitigation of foam built-up in the interior space of the bioreactor during use of the bioreactor for culturing of microorganisms or cells;
   wherein the coupling element further includes a portion of the casing that is substantially transmissive to ultrasound waves and is configured to allow ultrasonic waves generated by the foam mitigation device act upon foam built-up in the interior space of the bioreactor.

2. The bioreactor of claim 1, further comprising a stirring device extending through the second end of the casing and to a location between the first end and the intended fill height, wherein the stirring device is operative to rotate to stir the culture medium without direct mechanical agitation of the foam.

3. The bioreactor of claim 1, wherein the at least one coupling element is a plurality of coupling elements, each being adapted to receive one or more ultrasonic foam mitigation devices, wherein each coupling element of the plurality of coupling elements is positioned at a different respective location between the upper end and the lower end of the casing.

4. The bioreactor of claim 1, wherein the bioreactor is a single-use bioreactor adapted to be positioned within a bioreactor housing.

5. The bioreactor of claim 1, further comprising:
   at least one inlet port for introducing fluids into the interior space of the bioreactor; and
   at least one outlet port for removing fluids from the interior space of the bioreactor.

6. The bioreactor of claim 1, wherein the at least one coupling element comprises a plurality of coupling elements each provided at a different respective location between the intended filling height and the upper end of the casing;
   wherein each coupling element is adapted to receive and orient a respective mitigation device such that the mitigation device is configured to transmit ultrasonic waves with a main direction of propagation angled toward the lower end of the casing.

7. A system for culturing of microorganisms or cells comprising:
   a bioreactor for culturing of microorganisms or cells and for mitigating the accumulation of foam within the bioreactor via ultrasound and without the use of direct mechanical agitation, the bioreactor comprising:
      a casing defining an interior space of the bioreactor, the casing extending between a first, lower end and a second, upper end and including an intended filling height located between the first end and the second end, the casing including at least a portion that is substantially transmissive to ultrasound waves, and wherein said interior space is configured to receive and hold a culture medium with microbial or cellular liquid cultures;
      at least one inlet port for introducing gases and/or liquids into the interior space of the bioreactor;
      at least one outlet port for exhausting gases and/or removing liquids from the interior space of the bioreactor; and
   a foam mitigation device comprising an ultrasonic wave generator for generating ultrasonic waves, the foam mitigation device provided external to the casing and such that it is configured to transmit ultrasonic waves through a wall of the casing at a location between the intended filling height and the upper end, wherein said ultrasonic waves are configured to act upon foam built-up in the interior space of the bioreactor during use of the bioreactor for culturing of microorganisms or cells.

8. The system of claim 7, wherein the bioreactor further comprises a coupling element provided on the casing for coupling with the foam mitigation device for mitigation of foam built-up in the interior space of the bioreactor during use of the bioreactor for culturing of microorganisms or cells; and
   wherein the foam mitigation device is coupled with the coupling element.

9. The system of claim 7, wherein the bioreactor is a single-use bioreactor operative to be inserted within a bioreactor housing.

10. The system of claim 7, wherein the ultrasonic wave generator is oriented such that it transmits ultrasonic waves along a main direction of propagation that is angled toward the lower end of the casing.

11. The system of claim 7, wherein the ultrasonic wave generator is configured to generate an ultrasonic wave beam, wherein said ultrasonic wave beam has a substantially planar fan-like shape.

12. The system of claim 7, wherein the foam mitigation device comprises a plurality of ultrasonic wave generators, each positioned at a different respective height between the upper end and the lower end or location around a circumference of the casing.

13. The system of claim 12, wherein the plurality of ultrasonic wave generators are configured to generate ultrasonic waves each having different wavelengths.

14. The system of claim 7 further comprising a stirring device extending through the second end of the casing and to a location between the first end and the intended fill height, wherein the stirring device is operative to rotate to stir the culture medium without direct mechanical agitation of the foam.

15. A method of foam mitigation in bioreactors for culturing of microorganisms or cells comprising the steps of:

culturing of microorganisms or cells in a casing of a bioreactor, wherein the casing of the bioreactor comprises at least one ultrasonically transmissive part being configured to allow ultrasonic waves to enter the interior of the bioreactor; and  generating ultrasonic waves via an ultrasonic wave generator mounted external to the casing at a location between a fill height of a culture medium and an upper end of the casing, wherein the ultrasonic waves have a main direction of propagation that extends through the at least one ultrasonically transmissive part and at an angle that is oriented away from the upper end of the casing and such that the and pointing said ultrasonic waves are directed toward foam built-up inside the bioreactor.

16. The method of claim 15, further comprising the step of providing a single-use bioreactor.

17. The method of claim 15, further comprising the step of providing a bioreactor having:

at least one inlet port for introducing a fluid into the interior space of the bioreactor; and  at least one outlet port for removing a fluid from the interior space of the bioreactor.

* * * * *